United States Patent [19]
Bandman et al.

[11] Patent Number: 6,001,593
[45] Date of Patent: Dec. 14, 1999

[54] HUMAN MYOSIN HEAVY CHAIN-LIKE PROTEINS

[75] Inventors: Olga Bandman, Mountain View; Henry Yue, Sunnyvale; Neil C. Corley, Mountain View; Purvi Shah, Sunnyvale, all of Calif.

[73] Assignee: Incyte Pharmaceuticals, Inc., Palo Alto, Calif.

[21] Appl. No.: 08/966,318

[22] Filed: Nov. 7, 1997

[51] Int. Cl.$^6$ ............................ C12P 21/06; C12N 15/00; C07H 17/00
[52] U.S. Cl. .................... 435/69.1; 435/325; 435/252.3; 435/320.1; 536/23.1
[58] Field of Search .................................. 435/69.1, 325, 435/252.3, 320.1; 536/23.1

[56] References Cited

PUBLICATIONS

Martin, A.F. et al., "C-terminal Isoforms of the Myosin Heavy Chain and Smooth Muscle Function," *Comp. Biochem. Physiol.*, 117B(1):3–11 (1997).

Nieznanski, K. and Sobieszek, A., "Telokin (kinase-related protein) modulates the oligomeric state of smooth-muscle myosin light-chain kinase and its interaction with myosin filaments," *Biochem J.*, 322(1):65–71 (1997).

Sutherland, C., et al., "Phosphorylation of caldesmon by smooth-muscle casein kinase II," *Journal of Muscle Research and Cell Motility*, 15:440–456 (1994).

Li, H., et al., "Multiple Substrates for cGMP-Dependent Protein Kinase from Bovine Aortic Smooth Muscle; Purification of P132," *J. Vas. Res.*, 33(2):99–110 (1996).

Wilson, R., et al., "2.2 Mb of contiguous nucleotide sequence from chromosome III of *C. elegans,*" *Nature*, 368:32–38 (1994) (GI 532467).

Nasmyth, K. and Jansen, R, "The cytoskeleton in mRNA localization and cell differentiation," *Curr Opin Cell Biol.*, 9(3):396–400 (1997).

Abchee, A. and Marian, A.J, "Prognostic Significance of β–Myosin Heavy Chain Mutations is Reflective of Their Hypertrophic Expressivity in Patients with Hypertrophic Cardiomyopathy," *J. Investig. Med.*, 45(4):191–196 (1997).

Wakasaki, H., et al., "Targeted overexpression of protein kinase C β2 isoform in myocardium causes cardiomyopathy," *Proc. Natl. Acad. Sci. USA*, 94(17):9320–9325 (1997).

Bierhoff, E., et al., "Morphological Analogies of Fetal Prostate Stroma and Stromal Nodules in BPH," *The Prostate*, 31(4):234–240 (1997).

Wilson, R., et al., (GI 532467), GenBank sequence Database (Accession U13643), National Center for Biotechnology Information, National Library of Medicine, Bethesda, Maryland, 20894 (GI 532473).

Ho, G. and Chisholm R.L., "Substitution Mutations in the Myosin Essential Light Chain Lead to Reduced Actin–activated ATPase Activity Despite Stoichiometric Binding to the Heavy Chain," *The Journal of Biological Chemistry*, 272(7):4522–4527 (1997).

*Primary Examiner*—Karen Cochrane Carlson
*Attorney, Agent, or Firm*—Incyte Pharmaceuticals, Inc.

[57] ABSTRACT

The invention provides human myosin heavy chain-like proteins (MHCP) and polynucleotides which identify and encode MHCP. The invention also provides expression vectors, host cells, antibodies, agonists, and antagonists. The invention also provides methods for treating disorders associated with expression of MHCP.

8 Claims, 13 Drawing Sheets

```
             9        18        27        36        45        54
5' GT ACT TCT CTG CTA CCT TTC ACC TGC TCT TTT TCT GTG CCA TTG TTT CCC TTG
                  63        72        81        90        99       108
   CTA CCT TAC CTA AAA CCA GGC CCT AGA GAA ACA GAA AGA ATA CAT TGC CTG CCT
                 117       126       135       144       153       162
   TAG GAA TGA GCG AGA TAT GCT CAG AGA GGA GCT GGC TGA CCT GCA GGA GAC AGT
                 171       180       189       198       207       216
   GAA GAC GGG AGA GGT ATG TTA GCA TTA GCC TGG AAT TCA GGT CCC TCA CTG TTT
                 225       234       243       252       261       270
   TAC TCT CTA TCT TCC CTT TCA TGC CAT CTT TCC TAG CCT AAA TAC CTG AAA
                 279       288       297       306       315       324
   CTA CAG TGT TTA TTC TCT AAT CCA GAT TTG GTA GGT TGA AGC TAT TTC TTA CAC
                 333       342       351       360       369       378
   AGA GCT ATA TTT CAT GTA ACT GAT TCT AAC CAG GTT TTA CCT GTA GCA AAC ATG
                                                                       M
                 387       396       405       414       423       432
   TAT TGT TGC AGA GTG ACC TCA CAG AGC TTA CAG CTT CCA TAT GGG CCT TTT GTG
    Y   C   C   R   V   T   S   Q   S   L   Q   L   P   Y   G   P   F   V
```

FIGURE 1A

```
     441              450              459              468              477              486
ATG  GTG  GGT  TTT  TCC  CCC  CTG  CAG  AAA  CAT  GGC  TTA  GTT  ATA  ATC  CCC  GAT  GGC
 M    V    G    F    S    P    L    Q    K    H    G    L    V    I    I    P    D    G 495              504              513              522              531              540
ACT  CCC  AAT  GGT  GAT  GTC  AGT  CAT  GAA  CCA  GTG  GCT  GGA  GCC  ATC  ACT  GTT  GTG
 T    P    N    G    D    V    S    H    E    P    V    A    G    A    I    T    V    V 549              558              567              576              585              594
TCT  CAG  GAA  GCT  GCT  CAG  GTC  TTG  GAG  TCA  GCA  GGA  GAA  GGG  CCA  TTA  GAT  GTA
 S    Q    E    A    A    Q    V    L    E    S    A    G    E    G    P    L    D    V 603              612              621              630              639              648
AGG  CTA  CGA  AAA  CTT  GCT  GCT  GGA  GAG  GAA  AAG  GAA  CAG  CTA  CTG  TCA  ATT  AGA  AAA
 R    L    R    K    L    A    A    G    E    E    K    E    Q    L    L    S    I    R    K 657              666              675              684              693              702
CTG  AAG  CTT  CAG  TTA  GAG  GAG  GAA  CGA  CAG  AAA  TGC  TCC  AGG  AAT  GAT  GGC  ACA
 L    K    L    Q    L    E    E    E    R    Q    K    C    S    R    N    D    G    T 711              720              729              738              747              756
GTG  GGT  GAC  CTG  GCA  GGA  CTG  CAG  AAT  GGC  TCA  GAC  TTG  CAG  TTC  ATC  GAA  ATG
 V    G    D    L    A    G    L    Q    N    G    S    D    L    Q    F    I    E    M 765              774              783              792              801              810
CAG  AGA  GAT  GCC  AAT  AGA  CAA  ATT  AGC  GAA  TAC  AAA  TTT  AAG  CTT  TCA  AAA  GCA
 Q    R    D    A    N    R    Q    I    S    E    Y    K    F    K    L    S    K    A
```

FIGURE 1B

```
       819             828             837             846             855             864
GAA CAG GAT ATA ACT ACC TTG GAG CAA AGT ATT AGC CGG CTT GAG GGA CAG GTT
 E   Q   D   I   T   T   L   E   Q   S   I   S   R   L   E   G   Q   V 873             882             891             900             909             918
CTG AGA TAT AAA ACT GCT GCT GAG AAT GCT GAG AAA GTT GAA GAT GAA TTG AAA
 L   R   Y   K   T   A   A   E   N   A   E   K   V   E   D   E   L   K 927             936             945             954             963             972
GCA GAA AAA CGG AAG CTA CAA CGA GAG TTA CGA ACA GCA CTG GAC AAG ATT GAG
 A   E   K   R   K   L   Q   R   E   L   R   T   A   L   D   K   I   E 981             990             999            1008            1017            1026
GAG ATG GAG ATG ACC AAC AGC CAC CTG GCC AAG CGG CTG GAG AAG ATG AAG GCC
 E   M   E   M   T   N   S   H   L   A   K   R   L   E   K   M   K   A 1035            1044            1053            1062            1071            1080
AAT AGG ACA GCA CTT CTG GCC CAG CAG TAG GAA AAC CAC CCT TCA ACC TGG GTG
 N   R   T   A   L   L   A   Q   Q 1089            1098            1107            1116            1125            1134
ATG CTC CTT GGG GCC CTA CCT AGA GGG ACT GAC TTT TGT CCA TTG ACA CAA ACC 1143            1152            1161            1170            1179            1188
CCT TTT AGT ACT GTT TTG AGT TTT GTC ATT AAA ACA GCC ACC TTT GTA TTT TAT
```

FIGURE 1C

```
1197           1206           1215           1224           1233           1242
AAT TTA TGA CAG AAT GAA GTC ATT TTG AAT CTA CAT GAA TGA ACA CTT TGG ATT
           1251           1260           1269           1278           1287           1296
TTG TTG TAG TTT GAT TCT AGG GTA GAA CCA GTC CAT GCT GTT TTT ATT TTT TAT
           1305           1314           1323           1332           1341           1350
CTC CGT AAT TGT AGA ATC ATG TTT ACT CAA CGT TTT TCC CCA GCT GCC TCA GTA
           1359           1368           1377           1386           1395           1404
ACT GGG CAC TCG GAG GCC TTG GCA CGG GTT CTG GAG GAC AGA CAG CAA TTC TAT
           1413           1422           1431           1440           1449           1458
GAG TGC TCA CTG AGA TAC TTG CTG GAG ACC TCA GAA AAC ACA AGT GCC TTC TCC
           1467           1476           1485           1494           1503           1512
ACG GTG CAA TTC AGA CTT CAG TGA TCT CCA GTG GTC AAA AGA CAT TTA CCC TTA
           1521           1530           1539           1548           1557           1566
ATA TCA GAC AAC ATT TAT ATT TTA GTG AAG AAA CAA GTT CTC GGG TGG GGA ATC
           1575           1584           1593           1602           1611           1620
TAT GTT TCA CTC AGA TTT ATA TGT TTG GAG GAA AAA AGC CTT TTT TTG TAA AAT
           1629           1638           1647           1656           1665           1674
ATT TAA ATT TAT ATA AGA AAA TGT TAG AAA AAA ATA TGG GGA GTG TAT ATA AAA
```

FIGURE 1D

```
           1683        1692        1701        1710        1719        1728
     CTT GCT TTA TTG CAT GGG GCA GGG GAA GTC CAG GCC TAA TAC TCC TAA AGT AAG
         1737        1746        1755        1764        1773        1782
     AGT TGG GTC CTT TTT TTC TTC AAT ACA ACT GTG CTG TAC CTT GTA AAG TAT TTT
         1791        1800        1809        1818        1827        1836
     ATC TGC TGC TTA TTT GTG GAA TGA AAC CTC AAA CAA ACC CAA AGG GGG AGG GTA
         1845        1854        1863        1872        1881        1890
     GGG CAG GGC AGG CAG ATT GGA AAT CTG CCT GCA GAT TCT ATT AAA TAC ACC CTT
         1899        1908        1917        1926        1935        1944
     TTG CCA ACC AAA AAA AAA AAG GTT AAA AAA AGC GAA ACA GGG TGG TCT GTA TAG
         1953        1962        1971        1980        1989        1998
     GGA CAG GAA AGG AAA AAA AAG GGG GGG CCC CCG AAT TTT GGG ACC CCT CGC
         2007        2016        2025        2034        2043        2052
     CCC GGG GAA TTA TTT CCG GGC CGG GTT CCT GGA GGG GTA CCA TTT TTC CCT AAA
         2061        2070        2079        2088        2097
     AGG GAG GCC GTT TTA ACC GCC TGG GGG TAA TCC AGG GCC AAG GTG TTT TTC  3'
```

FIGURE 1E

```
                                                                                    54
5' AA AGC CGG GAG ATC GAC TGT TTG AGC CCG GAA GCG CAG AAG CTG GCG GAA GCC

108
CGG CTC GCT GCA AAA CGG GCG GCC CGC GAG GCG GAG ATC CGC ATG AAG
                                                                          M   K

162
GAG CTG GAG CGG CAG CAG AAG GAG GTA GAA GAG AGA CCA GAA AAA GAT TTT ACT
 E   L   E   R   Q   Q   K   E   V   E   E   R   P   E   K   D   F   T

216
GAG AAG GGG ACT TCT CGT AAC ATG CCG GGC CTG TCT GCA GCC ACG CTG GCC TCT CTG
 E   K   G   T   S   R   N   M   P   G   L   S   A   A   T   L   A   S   L

270
GGT GGG ACT TCC TCT CGG AGA GGC AGC GGA GAC ACC TCC ATC TCC ATC GAC ACC
 G   G   T   S   S   R   R   G   S   G   D   T   S   I   S   I   D   T

324
GAG GCA TCC ATC AGG GAA ATC AAG GAC TCT CTA GCA GAA GTT GAA AAG TAT
 E   A   S   I   R   E   I   K   D   S   L   A   E   V   E   K   Y

378
AAG AAG GCT ATG GTT TCC AAT GCT CAG CTA GAC AAT GAA AAG ACA AAC TTC ATG
 K   K   A   M   V   S   N   A   Q   L   D   N   E   K   T   N   F   M
```

FIGURE 2A

```
      387           396           405           414           423           432
TAC CAG GTT GAT ACC CTA AAA GAT ATG TTG CTG GAG CTT GAA CAG CTG GCT
 Y   Q   V   D   T   L   K   D   M   L   L   E   L   E   Q   L   A 441           450           459           468           477           486
GAA TCT AGG CGG CAG TAC GAA GAG AAA AAC TTT GAA TTT GAA AGG GAA AAA CAC
 E   S   R   R   Q   Y   E   E   K   N   F   E   F   E   R   E   K   H 495           504           513           522           531           540
GCC CAC AGT ATA CTG CAA TTT CAG TTT GCT GAA GTC AAG GAG GCC CTG AAG CAA
 A   H   S   I   L   Q   F   Q   F   A   E   V   K   E   A   L   K   Q 549           558           567           576           585           594
AGA GAG ATG CTC GAG AAA CAT GGA ATA ATC CTA AAT TCA GAA ATA GCT ACC
 R   E   M   L   E   K   H   G   I   I   L   N   S   E   I   A   T 603           612           621           630           639           648
AAT GGA GAG ACT TCC GAC ACC CTC AAT AAT GTT GGA TAC CAA GGT CCT ACC AAG
 N   G   E   T   S   D   T   L   N   N   V   G   Y   Q   G   P   T   K 657           666           675           684           693           702
ATG ACA AAA GAA GAG TTA AAT GCC CTC AAG TCG ACA GGG GAT GGG ACC CTA GAT
 M   T   K   E   E   L   N   A   L   K   S   T   G   D   G   T   L   D 711           720           729           738           747           756
ATT AGG TTG AAA AAG CTG GTT GAT GAA CGG GAA TGC TTA TTG GAA CAG ATT AAG
 I   R   L   K   K   L   V   D   E   R   E   C   L   L   E   Q   I   K
```

FIGURE 2B

```
      765            774            783            792            801            810
AAA CTC AAA GGG CAG CTG GAG GAG AGA CAG AAG ATT GGC AAA CTA GAC AAT CTT
 K   L   K   G   Q   L   E   E   R   Q   K   I   G   K   L   D   N   L 819            828            837            846            855            864
CGA TCT GAA GAT GAT GTC TTG GAA AAC GGG ACA GAC ATG CAT GTA ATG GAC CTA
 R   S   E   D   D   V   L   E   N   G   T   D   M   H   V   M   D   L 873            882            891            900            909            918
CAA AGG GAT GCC AAC AGA CAG ATC AGC GAC CTC AAA TTT AAA CTT GCA AAA TCT
 Q   R   D   A   N   R   Q   I   S   D   L   K   F   K   L   A   K   S 927            936            945            954            963            972
GAG CAA GAG ATA ACT GCA TTA GAA CAA AAT GTA ATA AGG TTA GAG AGT CAA GTA
 E   Q   E   I   T   A   L   E   Q   N   V   I   R   L   E   S   Q   V 981            990            999           1008           1017           1026
TCA CGT TAC AAA TCA GCG GCT GAA AAT GCA GAA AAA ATA GAA GAT GAA CTT AAG
 S   R   Y   K   S   A   A   E   N   A   E   K   I   E   D   E   L   K 1035           1044           1053           1062           1071           1080
GCA GAA AAA CGG AAA CTC CAA AGA GAG CTC CGC TCT GCA TTG GAT AAA ACA GAA
 A   E   K   R   K   L   Q   R   E   L   R   S   A   L   D   K   T   E 1089           1098           1107           1116           1125           1134
GAG CTC GAG GTG AGC AAC GGC CAC TTA GTG AAG CGT CTG GAA AAA ATG AAA GCA
 E   L   E   V   S   N   G   H   L   V   K   R   L   E   K   M   K   A
```

FIGURE 2C

```
              1143            1152            1161            1170            1179            1188
       AAT CGG AGT GCA CTC TTG TCC CAG CAG TAA ATT CCA GCT CTG ATC AGG CAA CTG
        N   R   S   A   L   L   S   Q   Q 1197            1206            1215            1224            1233            1242
       GTT GGT GAC TGG AGA GCA TTG TTT CAT AGG CTT TTC TCT GTC CTG TCT GGG AGC 1251            1260            1269            1278            1287            1296
       GCT GCT TCT TCC CCT GCC TTC TGA GAG ACG AAG ACC GTG GCG AGC TTG GCG CTT 1305            1314            1323            1332            1341            1350
       AGG GGC TCC CGT GCC ATG GCT CAC CCC AGG GAG CCC CAG CAG CCA CCA GGT GCC 1359            1368            1377            1386            1395            1404
       TCT GTC TGC AGA CCC CTG GCC CGG GCT GGC GCC GAC GCT CAG AAC CTG CAG GTA 1413            1422            1431            1440            1449            1458
       CTT CAT AAG CAC ACA GGG GCC TCG AGG GAG CTC TGT GTC TGA CCG CAC AGC AGC 1467            1476            1485            1494            1503            1512
       CTC TGA ATG CCG CTG GAA GTG ATG ATC AAA GTA AAG ATT CAG TTG GGA CTT GAG 1521            1530            1539            1548            1557            1566
       TTT TTT TTT TCA TGT GTC TTG CTG AAG ATT AAG GGG AAA TGT TAC AGT GTT 1575            1584            1593            1602            1611            1620
       GGG ACT TCC TTT CAT GGC AGA ATC TAC AAT TTG AGC GAC TTC AGT AGT ATC TCT
```

FIGURE 2D

```
     1629          1638          1647          1656          1665          1674
TAG TCT ACG CTT TTC ATA CAC AAA ACA CTG TGG AAC CAC AAG CCA TTA CCA AGC
     1683          1692          1701          1710          1719          1728
AAA ACT CTT TCA CTG GAA ACA AGG GGG CAG TCT AGA AGT AAA AGT GAC CTT AAG
     1737          1746          1755          1764          1773          1782
AAG ACT CTT TAC AGG CAA ATG CAA CTT TTC TAA GGG ATT TTT GCA TCA GTT
     1791          1800          1809          1818          1827          1836
CAG TCA TAA GAA TAC TTT TTT CCA GGG TAA TTA GGC AAT AGC TTC ACT GAA AAT
     1845          1854          1863          1872          1881          1890
GAC AGC TTT TCA TTG CAT TAT TAT TTA ATC CTT ATA TTT GGA ATT GAA GTC GTT AAC
     1899          1908          1917          1926          1935          1944
TTC TTT TAA AGA ATG TAC TAT TAG AAA AAT TAA AAA TGA AAT GTT GAG AGA CTT
     1953          1962
CAA AAA AAA AAA AAA AAA AAA AAA AA 3'
```

```
1    MKELERQQKEVEERPEKDFT    3440902
1    M-------------------    GI 532473

21   EKGSRNMPGLSAATLASLGG    3440902
2    --------------------    GI 532473

41   TSSRRGSGDTSISIDTEASI    3440902
2    --------------------    GI 532473

61   REIKDSLAEVEEKYKKAMVS    3440902
2    --------------------    GI 532473

81   NAQLDNEKTNFMYQVDTLKD    3440902
2    --------------------    GI 532473

101  MLLELEEQLAESRRQYEEKN    3440902
2    ------------RKDYEELE    GI 532473

121  KEFEREKHAHSILQFQFAEV    3440902
10   QTIYTQRHARNA--------    GI 532473

141  KEALKQREEMLEKHGIILNS    3440902
22   ----RDSANVIPNQGVD---    GI 532473

161  EIATNGETSDTLNNVGYQGP    3440902
35   --------------------    GI 532473

181  TKMTKEELNALKSTGDGTLD    3440902
35   --------------------    GI 532473

201  IRLKKLVDERECLLEQIKKL    3440902
35   --------------------    GI 532473

221  KGQLEERQKIGKLDNLRSED    3440902
35   --------------------    GI 532473
```

FIGURE 4A

```
241  DVLENGTDMHVMDLQRDANR           3440902
35   -----------DVNKDAAK            GI 532473

261  QISDLKFKLAKSEQEITALE           3440902
43   QLAEMKLKMQDLERENTNQQ           GI 532473

281  QNVIRLESQVSRYKSAAENA           3440902
63   GNVIRMEGQMKRYKSNADVA           GI 532473

301  EKIEDELKAEKRKLQRELRS           3440902
83   EKELDELKTQMRQTKKELRD           GI 532473

321  ALDKTEELEVSNGHLVKRLE           3440902
103  KENALDEQKETNKHLQSRLE           GI 532473

341  KMKANRSALLSQQ                  3440902
123  KMRMQRTG--RPL                  GI 532473
```

FIGURE 4B

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 226 amino acids
        (B) TYPE: amino acid
        (C) STRANDEDNESS: single
        (D) TOPOLOGY: linear (vii) IMMEDIATE SOURCE:
        (A) LIBRARY: LUNGNOT18
        (B) CLONE: 2220246

(xi) SEQUENCE DESCRIPTION: SEQ ID NO:1:

```
Met Tyr Cys Cys Arg Val Thr Ser Gln Ser Leu Gln Leu Pro Tyr Gly
 1               5                  10                  15

Pro Phe Val Met Val Gly Phe Ser Pro Leu Gln Lys His Gly Leu Val
                20                  25                  30

Ile Ile Pro Asp Gly Thr Pro Asn Gly Asp Val Ser His Glu Pro Val
                35                  40                  45

Ala Gly Ala Ile Thr Val Val Ser Gln Glu Ala Ala Gln Val Leu Glu
 50                  55                  60

Ser Ala Gly Glu Gly Pro Leu Asp Val Arg Leu Arg Lys Leu Ala Gly
65                   70                  75                  80

Glu Lys Glu Glu Leu Leu Ser Gln Ile Arg Lys Leu Lys Leu Gln Leu
                85                  90                  95

Glu Glu Glu Arg Gln Lys Cys Ser Arg Asn Asp Gly Thr Val Gly Asp
                100                 105                 110

Leu Ala Gly Leu Gln Asn Gly Ser Asp Leu Gln Phe Ile Glu Met Gln
                115                 120                 125

Arg Asp Ala Asn Arg Gln Ile Ser Glu Tyr Lys Phe Lys Leu Ser Lys
    130                 135                 140

Ala Glu Gln Asp Ile Thr Thr Leu Glu Gln Ser Ile Ser Arg Leu Glu
145                 150                 155                 160

Gly Gln Val Leu Arg Tyr Lys Thr Ala Ala Glu Asn Ala Glu Lys Val
                165                 170                 175

Glu Asp Glu Leu Lys Ala Glu Lys Arg Lys Leu Gln Arg Glu Leu Arg
                180                 185                 190

Thr Ala Leu Asp Lys Ile Glu Glu Met Glu Met Thr Asn Ser His Leu
                195                 200                 205

Ala Lys Arg Leu Glu Lys Met Lys Ala Asn Arg Thr Ala Leu Leu Ala
    210                 215                 220

Gln Gln
225
```

-continued (2) INFORMATION FOR SEQ ID NO:2:

(i) SEQUENCE CHARACTERISTICS:
        (A) LENGTH: 2102 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT18
        (B) CLONE: 2220246

(xi) SEQUENCE DESCRIPTION: SEQ ID NO:2:

```
GTACTTCTCT GCTACCTTTC ACCTGCTCTT TTTCTGTGCC ATTGTTTCCC TTGCTACCTT     60
ACCTAAAACC AGGCCCTAGA GAAACAGAAA GAATACATTG CCTGCCTTAG GAATGAGCGA    120
GATATGCTCA GAGAGGAGCT GGCTGACCTG CAGGAGACAG TGAAGACGGG AGAGGTATGT    180
TAGCATTAGC CTGGAATTCA GGTCCCTCAC TGTTTTACTC TCTATCTTCC TTCCTTTCAT    240
CCTGCCATCT TTCCTAGCCT AAATACAAAC TACAGTGTTT ATTCTCTAAT CCAGATTTGG    300
TAGGTTGAAG CTATTTCTTA CACAGAGCTA TATTTCATGT AACTGATTCT AACCAGGTTT    360
TACCTGTAGC AAACATGTAT TGTTGCAGAG TGACCTCACA GAGCTTACAG CTTCCATATG    420
GGCCTTTTGT GATGGTGGGT TTTTCCCCCC TGCAGAAACA TGGCTTAGTT ATAATCCCCG    480
ATGGCACTCC CAATGGTGAT GTCAGTCATG AACCAGTGGC TGGAGCCATC ACTGTTGTGT    540
CTCAGGAAGC TGCTCAGGTC TTGGAGTCAG CAGGAGAAGG GCCATTAGAT GTAAGGCTAC    600
GAAAACTTGC TGGAGAGAAG GAAGAACTAC TGTCACAGAT TAGAAAACTG AAGCTTCAGT    660
TAGAGGAGGA ACGACAGAAA TGCTCCAGGA ATGATGGCAC AGTGGGTGAC CTGGCAGGAC    720
TGCAGAATGG CTCAGACTTG CAGTTCATCG AAATGCAGAG AGATGCCAAT AGACAAATTA    780
GCGAATACAA ATTTAAGCTT TCAAAAGCAG AACAGGATAT AACTACCTTG GAGCAAAGTA    840
TTAGCCGGCT TGAGGGACAG GTTCTGAGAT ATAAAACTGC TGCTGAGAAT GCTGAGAAAG    900
TTGAAGATGA ATTGAAAGCA GAAAAACGGA AGCTACAACG AGAGTTACGA ACAGCACTGG    960
ACAAGATTGA GGAGATGGAG ATGACCAACA GCCACCTGGC CAAGCGGCTG GAGAAGATGA   1020
AGGCCAATAG GACAGCACTT CTGGCCCAGC AGTAGGAAAA CCACCCTTCA ACCTGGGTGA   1080
TGCTCCTTGG GGCCCTACCT AGAGGGACTG ACTTTTGTCC ATTGACACAA ACCCCTTTTA   1140
GTACTGTTTT GAGTTTTGTC ATTAAAACAG CCACCTTTGT ATTTTATAAT TTATGACAGA   1200
ATGAAGTCAT TTTGAATCTA CATGAATGAA CACTTTGGAT TTTGTTGTAG TTTGATTCTA   1260
GGGTAGAACC AGTCCATGCT GTTTTTATTT TTTATCTCCG TAATTGTAGA ATCATGTTTA   1320
CTCAACGTTT TTCCCCAGCT GCCTCAGTAA CTGGGCACTC GGAGGCCTTG GCACGGGTTC   1380
TGGAGGACAG ACAGCAATTC TATGAGTGCT CACTGAGATA CTTGCTGGAG ACCTCAGAAA   1440
ACACAAGTGC CTTCTCCACG GTGCAATTCA GACTTCAGTG ATCTCCAGTG GTCAAAAGAC   1500
ATTTACCCTT AATATCAGAC AACATTTATA TTTTAGTGAA GAAACAAGTT CTCGGGTGGG   1560
GAATCTATGT TTCACTCAGA TTTATATGTT TGGAGGAAAA AAGCCTTTTT TTGTAAAATA   1620
TTTAAATTTA TATAAGAAAA TGTTAGAAAA AAATATGGGG AGTGTATATA AAACTTGCTT   1680
TATTGCATGG GGCAGGGGAA GTCCAGGCCT AATACTCCTA AAGTAAGAGT TGGGTCCTTT   1740
TTTTCTTCAA TACAACTGTG CTGTACCTTG TAAAGTATTT TATCTGCTGC TTATTTGTGG   1800
AATGAAACCT CAAACAAACC CAAAGGGGGA GGGTAGGGCA GGGCAGGCAG ATTGGAAATC   1860
TGCCTGCAGA TTCTATTAAA TACACCCTTT TGCCAACCAA AAAAAAAAAG GTTAAAAAAG   1920
```

```
GCGAAACAGG GTGGTCTGTA TAGGGACAGG AAAGGAAAAA AAAAAAGGGG GGGCCCCCGA    1980

ATTTTGGGAC CCCTCGCCCC GGGGAATTAT TTCCGGGCCG GGTTCCTGGA GGGGTACCAT    2040

TTTTCCCTAA AAGGGAGGCC GTTTTAACCG CCTGGGGGTA ATCCAGGGCC AAGGTGTTTT    2100

TC                                                                   2102
```

(2) INFORMATION FOR SEQ ID NO:3:

(i) SEQUENCE CHARACTERISTICS:
        (A) LENGTH: 353 amino acids
        (B) TYPE: amino acid
        (C) STRANDEDNESS: single
        (D) TOPOLOGY: linear (vii) IMMEDIATE SOURCE:
        (A) LIBRARY: PENCNOT06
        (B) CLONE: 3440902

(xi) SEQUENCE DESCRIPTION: SEQ ID NO:3:

```
Met Lys Glu Leu Glu Arg Gln Gln Lys Glu Val Glu Arg Pro Glu
 1               5                  10                  15

Lys Asp Phe Thr Glu Lys Gly Ser Arg Asn Met Pro Gly Leu Ser Ala
                20                  25                  30

Ala Thr Leu Ala Ser Leu Gly Gly Thr Ser Ser Arg Arg Gly Ser Gly
            35                  40                  45

Asp Thr Ser Ile Ser Ile Asp Thr Glu Ala Ser Ile Arg Glu Ile Lys
        50                  55                  60

Asp Ser Leu Ala Glu Val Glu Glu Lys Tyr Lys Lys Ala Met Val Ser
65                  70                  75                  80

Asn Ala Gln Leu Asp Asn Glu Lys Thr Asn Phe Met Tyr Gln Val Asp
                85                  90                  95

Thr Leu Lys Asp Met Leu Leu Glu Leu Glu Glu Gln Leu Ala Glu Ser
               100                 105                 110

Arg Arg Gln Tyr Glu Glu Lys Asn Lys Glu Phe Glu Arg Glu Lys His
            115                 120                 125

Ala His Ser Ile Leu Gln Phe Gln Phe Ala Glu Val Lys Glu Ala Leu
        130                 135                 140

Lys Gln Arg Glu Glu Met Leu Glu Lys His Gly Ile Ile Leu Asn Ser
145                 150                 155                 160

Glu Ile Ala Thr Asn Gly Glu Thr Ser Asp Thr Leu Asn Asn Val Gly
                165                 170                 175

Tyr Gln Gly Pro Thr Lys Met Thr Lys Glu Glu Leu Asn Ala Leu Lys
            180                 185                 190

Ser Thr Gly Asp Gly Thr Leu Asp Ile Arg Leu Lys Lys Leu Val Asp
        195                 200                 205

Glu Arg Glu Cys Leu Leu Glu Gln Ile Lys Lys Leu Lys Gly Gln Leu
210                 215                 220

Glu Glu Arg Gln Lys Ile Gly Lys Leu Asp Asn Leu Arg Ser Glu Asp
225                 230                 235                 240

Asp Val Leu Glu Asn Gly Thr Asp Met His Val Met Asp Leu Gln Arg
                245                 250                 255

Asp Ala Asn Arg Gln Ile Ser Asp Leu Lys Phe Lys Leu Ala Lys Ser
            260                 265                 270

Glu Gln Glu Ile Thr Ala Leu Glu Gln Asn Val Ile Arg Leu Glu Ser
        275                 280                 285

Gln Val Ser Arg Tyr Lys Ser Ala Ala Glu Asn Ala Glu Lys Ile Glu
    290                 295                 300
```

-continued

```
Asp Glu Leu Lys Ala Glu Lys Arg Lys Leu Gln Arg Glu Leu Arg Ser
305                 310                 315                 320

Ala Leu Asp Lys Thr Glu Glu Leu Glu Val Ser Asn Gly His Leu Val
            325                 330                 335

Lys Arg Leu Glu Lys Met Lys Ala Asn Arg Ser Ala Leu Leu Ser Gln
            340                 345                 350

Gln
```

(2) INFORMATION FOR SEQ ID NO:4:

(i) SEQUENCE CHARACTERISTICS:
        (A) LENGTH: 1969 base pairs
        (B) TYPE: nucleic acid
        (C) STRANDEDNESS: single
        (D) TOPOLOGY: linear (vii) IMMEDIATE SOURCE:
        (A) LIBRARY: PENCNOT06
        (B) CLONE: 3440902

(xi) SEQUENCE DESCRIPTION: SEQ ID NO:4:

```
AAAGCCGGGA GATCGACTGT TTGAGCCCGG AAGCGCAGAA GCTGGCGGAA GCCCGGCTCG     60

CTGCAAAACG GGCGGCCCGC GCGGAGGCTC GCGAGATCCG CATGAAGGAG CTGGAGCGGC    120

AGCAGAAGGA GGTAGAAGAG AGACCAGAAA AAGATTTTAC TGAGAAGGGG TCTCGTAACA    180

TGCCGGGCCT GTCTGCAGCC ACGCTGGCCT CTCTGGGTGG GACTTCCTCT CGGAGAGGCA    240

GCGGAGACAC CTCCATCTCC ATCGACACCG AGGCATCCAT CAGGGAAATC AAGGACTCTC    300

TAGCAGAAGT TGAAGAGAAA TATAAGAAGG CTATGGTTTC CAATGCTCAG CTAGACAATG    360

AAAAGACAAA CTTCATGTAC CAGGTTGATA CCCTAAAAGA TATGTTGCTG GAGCTTGAAG    420

AACAGCTGGC TGAATCTAGG CGGCAGTACG AAGAGAAAAA CAAAGAATTT GAAAGGGAAA    480

AACACGCCCA CAGTATACTG CAATTTCAGT TTGCTGAAGT CAAGGAGGCC CTGAAGCAAA    540

GAGAGGAAAT GCTCGAGAAA CATGGAATAA TCCTAAATTC AGAAATAGCT ACCAATGGAG    600

AGACTTCCGA CACCCTCAAT AATGTTGGAT ACCAAGGTCC TACCAAGATG ACAAAAGAAG    660

AGTTAAATGC CCTCAAGTCG ACAGGGGATG GGACCCTAGA TATTAGGTTG AAAAAGCTGG    720

TTGATGAACG GGAATGCTTA TTGGAACAGA TTAAGAAACT CAAAGGGCAG CTGGAGGAGA    780

GACAGAAGAT TGGCAAACTA GACAATCTTC GATCTGAAGA TGATGTCTTG GAAAACGGGA    840

CAGACATGCA GTAATGGAC CTACAAAGGG ATGCCAACAG ACAGATCAGC GACCTCAAAT    900

TTAAACTTGC AAAATCTGAG CAAGAGATAA CTGCATTAGA ACAAAATGTA ATAAGGTTAG    960

AGAGTCAAGT ATCACGTTAC AAATCAGCGG CTGAAAATGC AGAAAAAATA GAAGATGAAC   1020

TTAAGGCAGA AAAACGGAAA CTCCAAAGAG AGCTCCGCTC TGCATTGGAT AAAACAGAAG   1080

AGCTCGAGGT GAGCAACGGC CACTTAGTGA AGCGTCTGGA AAAAATGAAA GCAAATCGGA   1140

GTGCACTCTT GTCCCAGCAG TAAATTCCAG CTCTGATCAG GCAACTGGTT GGTGACTGGA   1200

GAGCATTGTT TCATAGGCTT TTCTCTGTCC TGTCTGGGAG CGCTGCTTCT TCCCCTGCCT   1260

TCTGAGAGAC GAAGACCGTG GCGAGCTTGG CGCTTAGGGG CTCCCGTGCC ATGGCTCACC   1320

CCAGGGAGCC CCAGCAGCCA CCAGGTGCCT CTGTCTGCAG ACCCCTGGCC CGGGCTGGCG   1380

CCGACGCTCA GAACCTGCAG GTACTTCATA AGCACACAGG GGCCTCGAGG GAGCTCTGTG   1440

TCTGACCGCA CAGCAGCCTC TGAATGCCGC TGGAAGTGAT GATCAAAGTA AAGATTCAGT   1500

TGGGACTTGA GTTTTTTTTT TTTTCATGTG TCTTGCTGAA GATTAAGGGG AAATGTTACA   1560

GTGTTGGGAC TTCCTTTCAT GGCAGAATCT ACAATTTGAG CGACTTCAGT AGTATCTCTT   1620
```

-continued

```
AGTCTACGCT TTTCATACAC AAAACACTGT GGAACCACAA GCCATTACCA AGCAAAACTC  1680

TTTCACTGGA AACAAGGGGG CAGTCTAGAA GTAAAAGTGA CCTTAAGAAG ACTCTTTACA  1740

GGCAACAAAT GAAGCTTTTC TAAGGGATTT TTGCATCAGT TCAGTCATAA GAATACTTTT  1800

TTCCAGGGTA ATTAGGCAAT AGCTTCACTG AAAATGACAG CTTTTCATTG CATTATTTAA  1860

TCCTTATATT TGGAATTGAA GTCGTTAACT TCTTTTAAAG AATGTACTAT TAGAAAAATT  1920

AAAAATGAAA TGTTGAGAGA CTTCAAAAAA AAAAAAAAAA AAAAAAAA            1969

(2) INFORMATION FOR SEQ ID NO:5:

(i) SEQUENCE CHARACTERISTICS:
        (A) LENGTH: 133 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 532473

(xi) SEQUENCE DESCRIPTION: SEQ ID NO:5:

Met Arg Lys Asp Tyr Glu Glu Leu Glu Gln Thr Ile Tyr Thr Gln Arg
 1               5                  10                  15

His Ala Arg Asn Ala Arg Asp Ser Ala Asn Val Ile Pro Asn Gln Gly
                20                  25                  30

Val Asp Val Asn Lys Asp Ala Ala Lys Gln Leu Ala Glu Met Lys
        35                  40                  45

Leu Lys Met Gln Asp Leu Glu Arg Glu Asn Thr Asn Gln Gln Gly Asn
    50                  55                  60

Val Ile Arg Met Glu Gly Gln Met Lys Arg Tyr Lys Ser Asn Ala Asp
65                  70                  75                  80

Val Ala Glu Lys Glu Leu Asp Glu Leu Lys Thr Gln Met Arg Gln Thr
                85                  90                  95

Lys Lys Glu Leu Arg Asp Lys Glu Asn Ala Leu Asp Glu Gln Lys Glu
               100                 105                 110

Thr Asn Lys His Leu Gln Ser Arg Leu Glu Lys Met Arg Met Gln Arg
               115                 120                 125

Thr Gly Arg Pro Leu
               130
```

HUMAN MYOSIN HEAVY CHAIN-LIKE PROTEINS

FIELD OF THE INVENTION

This invention relates to nucleic acid and amino acid sequences of two human myosin heavy-chain-like proteins and to the use of these sequences in the diagnosis, prevention, and treatment of cell motility, reproductive, immunological, and neoplastic disorders.

BACKGROUND OF THE INVENTION

Cell motility is governed by the interaction between cytoskeletal proteins and other proteins embedded in the cell membranes. Cytoskeletal proteins which partake in the generation of force within the cell are termed contractile proteins. The energy source of such force generating activity is ATP.

Two predominant contractile proteins in all animal cells are actin and myosin. Actin is present in both soluble and polymerized forms. For example, filamentous (polymerized) actin interacts with myosin to contract or relax muscle tissues, to transport cell organelles through the intracellular medium, to cause cell movement, and to separate daughter nuclei during cytokinesis.

Myosin has a rodlike structure composed of heavy chain and light chain isoforms. Myosin light chains (MLCs) are associated stoichiometrically with the globular N-terminal domain of myosin heavy chains (MHCs). The globular domain also contains the ATP-binding and actin-binding sites. The MHC C-terminal domain structure is predominantly in the form of an α-helical coil, which interacts with the C-terminal domain of a second MHC monomer to form a coiled coil higher order structure. Heavy-chain isoforms appear to be present in all tissue types studied and may regulate maximum shortening velocity of the myofibrils and alter the sensitivity of actinomyosin to intracellular calcium ion concentrations. Two MHC isoforms expressed in smooth muscle are derived from alternate splicing that results in different amino acid sequences at their non-helical C-terminal regions. These sequences have been shown to interact with internal MHC amino acid residues and have a direct effect on crossbridge function and α-helical coiled coil formation (Martin, A. F. et al. (1997) Comp. Biochem. Physiol. B. Biochem. Mol. Biol. 117:3–11).

Vertebrate smooth muscle contraction is dependent upon levels of cAMP and intracellular calcium ions ($[Ca^{2+}]_i$). The sarcoplasmic reticulum (SR) serves as an intracellular store of $[Ca^{2+}]_i$. Following stimulation by second messenger molecules, such as inositoltrisphosphate, $[Ca^{2+}]_i$ is briefly released from the SR into the surrounding cytoplasm. $[Ca^{2+}]_i$ binds to calmodulin (CaM), which activates CaM-dependent myosin light chain protein kinase (MLCK). MLCK then phosphorylates MLC. In relaxed muscle, myosin is prevented from interacting with actin by tropomyosin. $Ca^{2+}$ binds to tropomyosin, causing a conformational change that leads to the release of actin. Phosphorylated MLC interacts with actin, forming actinomyosin, and initiates the contraction process. Muscle relaxation is brought about by active transport of $Ca^{2+}$ into the SR by a calcium ATPase pump, and MLCK is inactivated by a cAMP-dependent protein kinase. Interactions between these molecules may be modulated by other proteins. In particular, telokin, a kinase-related protein encoded by the 3' region of the vertebrate smooth muscle MLCK gene, inhibits MLCK-dependent phosphorylation of MLC by modulating the oligomeric state of MLCK and its interaction with dephosphorylated myosin filaments (Nieznanski, K. and Sobieszek, A. (1997) Biochem. J. 322:65–71). Phosphorylation of caldesmon by casein kinase II has been shown to regulate the interactions between caldesmon and smooth muscle myosin and the ability of caldesmon to cross-link actin and myosin filaments (Sutherland, C. et al. (1994) J. Muscle Res. Cell. Motil. 15:440–456). Elevation of intracellular cGMP and activation of protein kinase G (PKG) produces relaxation of smooth muscle. Thirty one potential PKG substrates have been identified, including a protein complex containing proteins of 40, 33, 28, and 20 kDa (Li, H. et al. (1996) J. Vasc. Res. 33:99–110).

A *Caenorhabditis elegans* gene which encodes a protein similar to the coiled coil domain of MHC has recently been identified, but a biochemical or physiological role has yet to be established (Wilson, R. et al. (1994) Nature 368:32–38). Nasmyth, K. and Jansen, R. P. (1997; Curr. Opin. Cell Biol. 9:396–400) have suggested that proteins of the cytoskeleton, including unconventional myosins, play active roles in the segregation of differentiation factors and mRNA species during oogenesis and cell differentiation.

Numerous pathologies have been associated with mutations encoded within MHC isoforms, with differential expression of myosin heavy chain isoforms, and with differential activation of enzymes which chemically modify myosin or myosin-associated proteins (Abchee, A. and Marian, A. J. (1997) J. Investig. Med. 45:191–196). For example, elevated levels of PKCβ2 isoform associated with diabetes mellitus increase transcriptional activation of the fetal myosin heavy chain gene in adult myocardium. Together with increases in transcriptional activation of other genes, such as atrial natriuretic factor, c-fos, transforming growth factor, and collagens, this may lead to cardiomyopathy (Wakasai, H. et al. (1997) Proc. Natl. Acad. Sci. 94:9320–9325). Stromal nodules in benign prostatic hyperplasia (BPH) have morphological, cytoskeletal, and biochemical similarities to fetal prostate stroma supporting the idea of a reactivation of fetal processes in BPH (Bierhoff, E. et al. (1997) Prostate 31:234–240).

The discovery of two new human myosin heavy chain-like proteins and the polynucleotides encoding them satisfies a need in the art by providing new compositions which are useful in the diagnosis, prevention and treatment of cell motility, reproductive, immunological, and neoplastic disorders.

SUMMARY OF THE INVENTION

The invention features two substantially purified polypeptides, human myosin heavy chain-like proteins collectively referred to as MHCP and individually referred to as MHCP-1 and MHCP-2, having at least one of the amino acid sequences selected from the group consisting of SEQ ID NO:1 and SEQ ID NO:3.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding MHCP-1 under conditions suitable for the expression of the polypeptide; and b) recovering the polypeptide from the host cell culture.

The invention also provides a pharmaceutical composition comprising a substantially purified MHCP-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing a cell motility disorder comprising administering to a subject in need of such treatment an effective amount of a pharmaceutical composition comprising purified MHCP-1.

The invention also provides a method for treating or preventing a reproductive disorder comprising administering to a subject in need of such treatment an effective amount of an antagonist to MHCP-1.

The invention also provides a method for treating or preventing an immunological disorder comprising administering to a subject in need of such treatment an effective amount of an antagonist to MHCP-1.

The invention also provides a method for treating or preventing a neoplastic disorder comprising administering to a subject in need of such treatment an effective amount of an antagonist to MHCP-1.

The invention also provides a method for detecting a polynucleotide which encodes MHCP-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding MHCP-1 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4 or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding MHCP-2 under conditions suitable for the expression of the polypeptide; and b) recovering the polypeptide from the host cell culture.

The invention also provides a pharmaceutical composition comprising a substantially purified MHCP-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for treating or preventing a cell motility disorder comprising administering to a subject in need of such treatment an effective amount of a pharmaceutical composition comprising purified MHCP-2.

The invention also provides a method for treating or preventing a reproductive disorder comprising administering to a subject in need of such treatment an effective amount of an antagonist to MHCP-2.

The invention also provides a method for treating or preventing an immunological disorder comprising administering to a subject in need of such treatment an effective amount of an antagonist to MHCP-2.

The invention also provides a method for treating or preventing a neoplastic disorder comprising administering to a subject in need of such treatment an effective amount of an antagonist to MHCP-2.

The invention also provides a method for detecting a polynucleotide which encodes MHCP-2 in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding MHCP-2 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of MHCP-1. The alignment was produced using MACDNASIS PRO software (Hitachi Software Engineering Co. Ltd. San Bruno, Calif.).

FIGS. 2A, 2B, 2C, 2D, and 2E show the amino acid sequence (SEQ ID NO:3) and nucleic acid sequence (SEQ ID NO:4) of MHCP-2. The alignment was produced using MACDNASIS PRO software (Hitachi Software Engineering Co. Ltd. San Bruno, Calif.).

FIG. 3 shows the amino acid sequence alignments between MHCP-1 (2220246; SEQ ID NO:1) and *Caenorhabditis elegans* myosin heavy chain-like protein (GI 532473; SEQ ID NO:5), produced using the multisequence alignment program of LASER GENE software (DNASTAR Inc, Madison Wis.).

FIGS. 4A and 4B show the amino acid sequence alignments between MHCP-2 (3440902; SEQ ID NO:3) and *Caenorhabditis elegans* myosin heavy chain-like protein (GI 532473; SEQ ID NO:5), produced using the multisequence alignment program of LASER GENE software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

MHCP, as used herein, refers to the amino acid sequences of substantially purified MHCP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to is MHCP, increases or prolongs the duration of the effect of MHCP. Agonists may include proteins, nucleic acids, carbohydrates, or any other molecules which bind to and modulate the effect of MHCP.

An "allele" or "allelic sequence", as used herein, is an alternative form of the gene encoding MHCP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding MHCP, as used herein include those with deletions, insertions, or substitutions of different nucleotides resulting in a polynucleotide that encodes the same or a functionally equivalent MHCP. Included within this definition are polymorphisms which may or may not be readily detectable using a particular oligonucleotide probe of the polynucleotide encoding MHCP, and improper or unexpected hybridization to alleles, with a locus other than the normal chromosomal locus for the polynucleotide sequence encoding MHCP. The encoded protein may also be "altered" and contain deletions, insertions, or substitutions of amino acid residues which produce a silent change and result in a functionally equivalent MHCP. Deliberate amino acid substitutions may be made on the basis of similarity in polarity, charge, solubility, hydrophobicity, hydrophilicity, and/or the amphipathic nature of the residues as long as the biological or immunological activity of MHCP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein refers to an oligopeptide, peptide, polypeptide, or protein sequence, and fragment thereof, and to naturally occurring or synthetic molecules. Fragments of MHCP are preferably about 5 to about 15 amino acids in length and retain the biological activity or the immunological activity of MHCP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to MHCP, decreases the amount or the duration of the effect of the biological or immunological activity of MHCP. Antagonists may include proteins, nucleic acids, carbohydrates, antibodies or any other molecules which decrease the effect of MHCP.

As used herein, the term "antibody" refers to intact molecules as well as fragments thereof, such as Fa, F(ab')$_2$, and Fv, which are capable of binding the epitopic determinant. Antibodies that bind MHCP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic MHCP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein refers broadly to any composition containing the given polynucleotide sequence. The composition may comprise a dry formulation or an aqueous solution. Compositions comprising polynucleotide sequences encoding MHCP or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding MHCP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to MHCP or the encoded MHCP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of MHCP. For example, modulation may cause an increase or a decrease in protein activity, binding characteristics, or any other biological, functional or immunological properties of MHCP.

"Nucleic acid sequence", as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length MHCP-1 and fragments thereof and a protein "comprising at least a portion of the amino acid sequence of SEQ ID NO:3" encompasses the full-length MHCP-2 and fragments thereof.

The term "sample", as used herein, is used in its broadest sense. A biological sample suspected of containing nucleic acid encoding MHCP, or fragments thereof, or MHCP itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of MHCP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

THE INVENTION

The invention is based on the discovery of two new human myosin heavy chain-like proteins, MHCP (MHCP-1 and MHCP-2), the polynucleotides encoding MHCP, and the use of these compositions for the diagnosis, prevention, or treatment of cell motility, reproductive, immunological, and neoplastic disorders.

Nucleic acids encoding the MHCP-1 of the present invention were first identified in Incyte Clone 2220246 from the lung cDNA library (LUNGNOT18) using a computer search for amino acid sequence alignments. A consensus sequence, SEQ ID NO:2, was derived from the following overlapping and/or extended nucleic acid sequences: Incyte Clones 2220246 (LUNGNOT18), 3176371 (UTRSTUT04), 1342768 (COLNTUT03), 158646 (ADENINB01), 1401623 (BRAITUT08), 1284678 (COLNNOT16), and 1887979 (BLADTUT07).

Nucleic acids encoding the MHCP-2 of the present invention were first identified in Incyte Clone 3440902 from the corpus cavemosum cDNA library (PENCNOT06) using a computer search for amino acid sequence alignments. A consensus sequence, SEQ ID NO:4, was derived from the following overlapping and/or extended nucleic acid sequences: Incyte Clones 3440902 (PENCNOT06), 3204018 (PENCNOT02), 2138118 (ENDCNOT01), 1352537 and 1402252 (LATRTUT02), 2098065 (BRAITUT02), 1805554 (SINTNOT13), and 1474994 (LUNGTUT03).

In one embodiment, the invention encompasses a polypeptide comprising the amino acid sequence of SEQ ID NO:1, as shown in FIGS. 1A, 1B, 1C, D, and 1E. MHCP-1 is 226 amino acids in length and has two potential glycosylation sites at residues N-118 and N-218, eight potential casein kinase II phosphorylation sites at residues S-65, S-104, T-109, S-143, T-150, S-157, T-168, and T-193, and a leucine zipper between residues L-71 and L-92. As shown in FIG. 3, MHCP-1 has chemical and structural homology with *Caenorhabditis elegans* myosin heavy chain-like protein (GI 532473; SEQ ID NO:5). In particular, MHCP-1 and C. elegans myosin heavy chain-like protein share 28% identity and one casein kinase II phosphorylation site. Northern analysis shows the expression of this sequence in various libraries, at least 48% of which are immortalized or cancerous and at least 23% of which involve immune response. Of particular note is the expression of MHCP-1 in lung, small intestine and colon, brain, uterus, ovary, prostate, and penile tissues.

In one embodiment, the invention encompasses a polypeptide comprising the amino acid sequence of SEQ ID NO:3, as shown in FIGS. 2A, 2B, 2C, 2D, and 2E. MHCP-2 is 354 amino acids in length and has two potential glycosylation sites at residues N-245 and N-345, one potential protein kinase A or G phosphorylation site at residue S-47, eleven potential casein kinase II phosphorylation sites at residues S-59, S-66, T-97, T-164, T-184, S-1 93, S-238, S-272, S-277, S-295, and S-320, six potential protein kinase C phosphorylation sites at residues T-20, S-42, S-43, S-59, T-97, and S-1 12, and one potential leucine zipper between residues L-199 and L-220. As shown in FIGS. 4A and 4B, MHCP-2 has chemical and structural homology with *C. elegans* myosin heavy chain-like protein (GI 532473; SEQ ID NO:5). In particular, MHCP-2 and *C. elegans* myosin heavy chain-like protein share 36% identity, and one casein kinase II phosphorylation site. Northern analysis shows the expression of this sequence in various libraries, at least 44% of which are immortalized or cancerous and at least 30% of which involve immune response. Of particular note is the expression of MHCP-2 in heart, lung, small intestine and colon, pancreas, bladder, breast, prostate, brain, and thyroid tissues, and in hematopoietic and muscle tissues.

The invention also encompasses MHCP variants. A preferred MHCP variant is one having at least 80%, and more preferably at least 90%, amino acid sequence identity to the MHCP amino acid sequence and retaining at least one biological, immunological, or other functional characteristic or activity of MHCP. A most preferred MHCP variant is one having at least 95% amino acid sequence identity to SEQ ID NO:1 or SEQ ID NO:3.

The invention also encompasses polynucleotides which encode MHCP. Accordingly, any nucleic acid sequence which encodes the amino acid sequence of MHCP can be used to produce recombinant molecules which express MHCP. In a particular embodiment, the invention encompasses the polynucleotide comprising the nucleic acid sequence of SEQ ID NO:2 as shown in FIGS. 1A, 1B, 1C, 1D, and 1E. In another embodiment, the invention encompasses the polynucleotide comprising the nucleic acid sequence of SEQ ID NO:4 as shown in FIGS. 2A, 2B, 2C, 2D, and 2E.

It will be appreciated by those skilled in the art that as a result of the degeneracy of the genetic code, a multitude of nucleotide sequences encoding MHCP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring MHCP, and all such variations are to be considered as being specifically disclosed.

Although nucleotide sequences which encode MHCP and its variants are preferably capable of hybridizing to the nucleotide sequence of the naturally occurring MHCP under appropriately selected conditions of stringency, it may be advantageous to produce nucleotide sequences encoding MHCP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MHCP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode MHCP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding MHCP or any fragment thereof.

Also encompassed by the invention are polynucleotide sequences that are capable of hybridizing to the claimed nucleotide sequences, and in particular, those shown in SEQ ID NO:2 or SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding MHCP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries (Clontech, Palo Alto, Calif.) to walk genomic DNA. This process avoids the need to screen libraries and is useful in finding intronlexon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode MHCP may be used in recombinant DNA molecules to direct expression of MHCP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express MHCP.

As will be understood by those of skill in the art, it may be advantageous to produce MHCP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter MHCP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding MHCP may be ligated to a heterologous sequence to encode a fusion protein. For example, to screen peptide libraries for inhibitors of MHCP activity, it may be useful to encode a chimeric MHCP protein that can be recognized by a commercially available antibody. A fusion protein may also be engineered to contain a cleavage site located between the MHCP encoding sequence and the heterologous protein sequence, so that MHCP may be cleaved and purified away from the heterologous moiety.

In another embodiment, sequences encoding MHCP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of MHCP, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of MHCP, or any part thereof, may be altered during direct synthesis and/or combined using chemical methods with sequences from other proteins, or any part thereof, to produce a variant polypeptide.

In order to express a biologically active MHCP, the nucleotide sequences encoding MHCP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding MHCP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding MHCP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORTI plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding MHCP, vectors based on SV40 or EBV may be used with an appropriate selectable marker.

In bacterial systems, a number of expression vectors may be selected depending upon the use intended for MHCP. For example, when large quantities of MHCP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding MHCP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding MHCP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express MHCP. For example, in one such system, *Autographa califomica* nuclear polyhedrosis virus (AcNPV) is used as a vector to express foreign genes in *Spodoptera frugiperda* cells or in Trichoplusia larvae. The sequences encoding MHCP may be cloned into a non-essential region of the virus, such as the polyhedrin gene, and placed under control of the polyhedrin promoter. Successful insertion of MHCP will render the polyhedrin gene inactive and produce recombinant virus lacking coat protein. The recombinant viruses may then be used to infect, for example, *S. frugiperda* cells or Trichoplusia larvae in which MHCP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding MHCP may be ligated into an adenovirus transcription/translation complex consisting of the late promoter and tripartite leader sequence. Insertion in a non-essential E1 or E3 region of the viral genome may be used to obtain a viable virus which is capable of expressing MHCP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding MHCP. Such signals include the ATG initiation codon and adjacent sequences. In cases where sequences encoding MHCP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express MHCP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding MHCP is inserted within a marker gene sequence, transformed cells containing sequences encoding MHCP can be identified by the absence of marker gene function. Alternatively, a marker gene can be placed in tandem with a sequence encoding MHCP under the control of a single promoter. Expression of the marker gene in response to induction or selection usually indicates expression of the tandem gene as well.

Alternatively, host cells which contain the nucleic acid sequence encoding MHCP and express MHCP may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding MHCP can be detected by DNA—DNA or DNA-RNA hybridization or amplification using probes or fragments or fragments of polynucleotides encoding MHCP. Nucleic acid amplification based assays involve the use of oligonucleotides or oligomers based on the sequences encoding MHCP to detect transformants containing DNA or RNA encoding MHCP.

A variety of protocols for detecting and measuring the expression of MHCP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on MHCP is preferred, but a competitive binding assay may be employed. These and other assays are described, among other places, in Hampton, R. et al. (1990*; Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding MHCP include oligolabeling, nick translation, end-labeling or PCR amplification using a labeled nucleotide. Alternatively, the sequences encoding MHCP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding MHCP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode MHCP may be designed to contain signal sequences which direct secretion of MHCP through a prokaryotic or eukaryotic cell membrane. Other constructions may be used to join sequences encoding MHCP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and MHCP may be used to facilitate purification. One such expression vector provides for expression of a fusion protein containing MHCP and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying MHCP from the fusion protein. A discussion of vectors which contain fusion proteins is provided in Kroll, D. J. et al. (1993; DNA Cell Biol. 12:441–453).

In addition to recombinant production, fragments of MHCP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of MHCP may be chemically synthesized separately and combined using chemical methods to produce the full length molecule.

THERAPEUTICS

Chemical and structural homology exists between MHCP-1 and *Caenorhabditis elegans* myosin heavy chain-like protein (GI 532473; SEQ ID NO:5). In addition, MHCP-1 is expressed in tumor and proliferating tissues, lung, small intestine and colon, brain, uterus, ovary, prostate, and penile tissues. Therefore, MHCP-1 appears to play a role in cell motility, reproductive, immunological, and neoplastic disorders.

Chemical and structural homology exists between MHCP-2 and *Caenorhabditis elegans* myosin heavy chain-like protein (GI 532473; SEQ ID NO:5). In addition, MHCP-2 is expressed in tumor and proliferating tissues, heart, lung, small intestine and colon, pancreas, bladder, breast, prostate, brain, and thyroid tissues, and in hematopoietic and muscle tissues. Therefore, MHCP-2 appears to play a role in cell motility, reproductive, immunological, and neoplastic disorders.

In one embodiment, MHCP or a fragment or derivative thereof may be administered to a subject to treat or prevent a cell motility disorder. Such disorders include, but are not limited to, ankylosing spondylitis, Chediak-Higashi syndrome, Duchenne and Becker muscular dystrophy, intrahepatic cholestasis, myocardial hyperplasia, cardiomyopathy, early onset periodontitis, cancers such as adenocarcinoma, ovarian carcinoma, and chronic myelogenous leukemia, and bacterial and helminth infections.

In another embodiment, a vector capable of expressing MHCP, or a fragment or a derivative thereof, may also be administered to a subject to treat or prevent a cell motility disorder including, but not limited to, those described above.

In still another embodiment, an agonist which modulates the activity of MHCP may also be administered to a subject to treat a cell motility disorder including, but not limited to, those described above.

In one embodiment, an antagonist of MHCP may be administered to a subject to prevent or treat a reproductive disorder. Such disorders may include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis; carcinoma of the male breast; and gynecomastia. In one aspect, an antibody which specifically binds MHCP may be used directly as an antagonist or indirectly as a targeting or delivery mechanism for bringing a pharmaceutical agent to cells or tissue which express MHCP.

In another embodiment, a vector expressing the complement of the polynucleotide encoding MHCP may be administered to a subject to treat or prevent a reproductive disorder including, but not limited to, those described above.

In one embodiment, an antagonist of MHCP may be administered to a subject to prevent or treat an immunological disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, and extracorporeal circulation; viral, bacterial, fungal, parasitic, protozoal, and helminthic infections; and trauma. In one aspect, an antibody which specifically binds MHCP may be used directly as an antagonist or indirectly as a targeting or delivery mechanism for bringing a pharmaceutical agent to cells or tissue which express MHCP.

In another embodiment, a vector expressing the complement of the polynucleotide encoding MHCP may be administered to a subject to treat or prevent an immunological disorder including, but not limited to, those described above.

In one embodiment, an antagonist of MHCP may be administered to a subject to prevent or treat a neoplastic disorder. Such disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds MHCP may be used directly as an antagonist or indirectly as a targeting or delivery mechanism for bringing a pharmaceutical agent to cells or tissue which express MHCP.

In another embodiment, a vector expressing the complement of the polynucleotide encoding MHCP may be administered to a subject to treat or prevent a neoplastic disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of MHCP may be produced using methods which are generally known in the art. In particular, purified MHCP may be used to produce antibodies or to screen libraries of pharmaceutical agents to identify those which specifically bind MHCP.

Antibodies to MHCP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with MHCP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to MHCP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of MHCP amino acids may be fused with those of another protein such as keyhole limpet hemocyanin and antibody produced against the chimeric molecule.

Monoclonal antibodies to MHCP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce MHCP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for MHCP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MHCP and its specific antibody. A two-site, monoclonal-based immunoassay utilizing monoclonal antibodies reactive to two non-interfering MHCP epitopes is preferred, but a competitive binding assay may also be employed (Maddox, supra).

In another embodiment of the invention, the polynucleotides encoding MHCP, or any fragment or complement thereof, may be used for therapeutic purposes. In one aspect, the complement of the polynucleotide encoding MHCP may be used in situations in which it would be desirable to block the transcription of the mRNA. In particular, cells may be transformed with sequences complementary to polynucleotides encoding MHCP. Thus, complementary molecules or fragments may be used to modulate MHCP activity, or to achieve regulation of gene function. Such technology is now well known in the art, and sense or antisense oligonucleotides or larger fragments, can be designed from various locations along the coding or control regions of sequences encoding MHCP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding MHCP. These techniques are described both in Sambrook et al. (supra) and in Ausubel et al. (supra).

Genes encoding MHCP can be turned off by transforming a cell or tissue with expression vectors which express high levels of a polynucleotide or fragment thereof which encodes MHCP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding MHCP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding MHCP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MHCP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of MHCP, antibodies to MHCP, mimetics, agonists, antagonists, or inhibitors of MHCP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of MHCP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example MHCP or fragments thereof, antibodies of MHCP, agonists, antagonists or inhibitors of MHCP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind MHCP may be used for the diagnosis of conditions or diseases characterized by expression of MHCP, or in assays to monitor patients being treated with MHCP, agonists, antagonists or inhibitors. The antibodies useful for diagnostic purposes may be prepared in the same manner as those described above for therapeutics. Diagnostic assays for MHCP include methods which utilize the antibody and a label to detect MHCP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring MHCP are known in the art and provide a basis for diagnosing altered or abnormal levels of MHCP expression. Normal or standard values for MHCP expression are established by combining body fluids or cell extracts taken from normal mammalian subjects, preferably human, with antibody to MHCP under conditions suitable for complex formation. The amount of standard complex formation may be quantified by various methods, but preferably by photometric means. Quantities of MHCP expressed in subject, control, and disease samples from biopsied tissues are compared with the standard values. Deviation between standard and subject values establishes the parameters for diagnosing disease.

In another embodiment of the invention, the polynucleotides encoding MHCP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of MHCP may be correlated with disease. The diagnostic assay may be used to distinguish between absence, presence, and excess expression of MHCP, and to monitor regulation of MHCP levels during therapeutic intervention.

In one aspect, hybridization with PCR probes which are capable of detecting polynucleotide sequences, including genomic sequences, encoding MHCP or closely related molecules, may be used to identify nucleic acid sequences which encode MHCP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding MHCP, alleles, or related sequences.

Probes may also be used for the detection of related sequences, and should preferably contain at least 50% of the nucleotides from any of the MHCP encoding sequences. The hybridization probes of the subject invention may be DNA or RNA and derived from the nucleotide sequence of SEQ ID NO:2 or SEQ ID NO:4 or from genomic sequence including promoter, enhancer elements, and introns of the naturally occurring MHCP.

Means for producing specific hybridization probes for DNAs encoding MHCP include the cloning of nucleic acid sequences encoding MHCP or MHCP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding MHCP may be used for the diagnosis of a disorder associated with expression of MHCP. Examples of such a disorder include, but are not limited to, a cell motility disorder such as ankylosing spondylitis, Chediak-Higashi syndrome, Duchenne and Becker muscular dystrophy, intrahepatic cholestasis, myocardial hyperplasia, cardiomyopathy, early onset periodontitis, cancers such as adenocarcinoma, ovarian carcinoma, and chronic myelogenous leukemia, and bacterial and helminth infections; a reproductive disorder such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis; carcinoma of the male breast; and gynecomastia; an immunological disorder such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, Werner syndrome, and autoimmune thyroiditis; complications of cancer, hemodialysis, and extracorporeal circulation; viral, bacterial, fungal, parasitic, protozoal, and helminthic infections; and trauma; and a neoplastic disorder such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding MHCP may be used in Southern or northern analysis, dot blot, or other membrane-based technologies; in PCR technologies; or in dipstick, pin, ELISA assays or microarrays utilizing fluids or tissues from patient biopsies to detect altered MHCP expression. Such qualitative or quantitative methods are well known in the art.

In a particular aspect, the nucleotide sequences encoding MHCP may be useful in assays that detect activation or induction of various cancers, particularly those mentioned above. The nucleotide sequences encoding MHCP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding MHCP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of MHCP, a normal or standard profile for expression is established. This may be accomplished by combining body fluids or cell extracts taken from normal subjects, either animal or human, with a sequence, or a fragment thereof, which encodes MHCP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MHCP may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of MHCP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode MHCP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding MHCP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, MHCP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between MHCP and the agent being tested, may be measured.

Another technique for drug screening which may be used provides for high throughput screening of compounds having suitable binding affinity to the protein of interest as described in published PCT application WO84/03564. In this method, as applied to MHCP large numbers of different small test compounds are synthesized on a solid substrate, such as plastic pins or some other surface. The test compounds are reacted with MHCP, or fragments thereof, and washed. Bound MHCP is then detected by methods well known in the art. Purified MHCP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MHCP specifically compete with a test compound for binding MHCP. In this manner, the antibodies can be used to detect the presence of any peptide which shares one or more antigenic determinants with MHCP.

In additional embodiments, the nucleotide sequences which encode MHCP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

LUNGNOT18

The LUNGNOT18 cDNA library was constructed from microscopically normal left upper lobe lung tissue removed from a 66-year-old Caucasian female during a segmental lung resection following a diagnosis of malignant lung neoplasm. Pathology for the associated tissue from the left upper lobe lung showed grade 2 adenocarcinoma with bronchoalveolar features and prominent inflammation forming a well-circumscribed nodular mass. The tumor did not involve the pleura. The bronchial margin was negative for tumor. Five intrapulmonary peribronchial lymph nodes, inferior mediastinal lymph nodes comprising 6 subcarinal lymph nodes, 2 left pulmonary artery lymph nodes, 2 left pulmonary artery lymph nodes, 4 left paratracheal lymph nodes, and 5 left bronchial lymph nodes were all negative for tumor. Patient history included cerebrovascular disease, atherosclerosis, pulmonary insufficiency, and a normal delivery. Previous surgery included endarterectomy. Patient medications included Trental® (pentoxifylline; Hoechst-Roussel Pharmaceuticals, Inc., Somerville, N.J.); Zocor; and EC-ASA. Family history included acute myocardial infarction in the mother and father and atherosclerosis in the sibling.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with phenol, pH 8.0, precipitated using 0.3 M sodium acetate and 2.5 volumes of ethanol, resuspended in RNAse-free water, and treated with DNase at 37° C. Extraction and precipitation were repeated as before. The mRNA was then isolated using the Qiagen OLIGOTEX kit (QIAGEN, Inc., Chatsworth, Calif.) and used to construct the cDNA library.

The RNA was handled according to the recommended protocols in the SUPERSCRIPT plasmid system (Catalog #18248-013; GIBCO-BRL). cDNA synthesis was initiated with a NotI-oligo d(T) primer. Double-stranded cDNA was blunted, ligated to EcoRI adaptors, digested with NotI, fractionated on a SEPHAROSE CL4B column (Catalog #275105, Pharmacia), and those cDNAs exceeding 400 bp were ligated into the NotI and EcoRI sites of the pINCY vector (Incyte pharmaceuticals, Palo Alto, Calif.). The plasmid pINCY was subsequently transformed into DH12S competent cells (Cat. #18312-017, GIBCO-BRL).

PENCNOT06

The PENCNOT06 cDNA library was constructed from penile corpora cavernosa tissue obtained from an African American male (specimen #1011B). Pathology indicated surgical margins were free of neoplasm. Pathology for the associated tumor tissue indicated invasive grade 4 (of 4) urothelial carcinoma forming a soft tissue scrotal mass that invaded the cavernous body of the penis and encased both testicles. The right inguinal lymph node showed metastatic grade 4 (of 4) urothelial carcinoma, with extranodal invasion.

The frozen tissue was homogenized and lysed in TRIZOL reagent (1 g tissue/10 ml TRIZOL; Cat. #10296-028; GIBCO-BRL), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. Extraction and precipitation were repeated as before. The mRNA was then isolated using the Qiagen OLIGOTEX kit (QIAGEN, Inc., Chatsworth, Calif.) and used to construct the cDNA library.

The mRNA was handled according to the recommended protocols in the SUPERSCRIPT plasmid system (Cat. #18248-013, GIBCO-BRL). cDNA synthesis was initiated with a NotI-oligo d(T) primer. Double-stranded cDNA was blunted, ligated to EcoRI adaptors, digested with NotI, fractionated on a SEPHAROSE CL4B column (Cat. #275105-01; Pharmacia), and those cDNAs exceeding 400 bp were ligated into the NotI and EcoRI sites of the pINCY vector (Incyte). The plasmid pINCY was subsequently transformed into DH5α competent cells (Cat. #18258-012; GIBCO-BRL).

II Isolation and Sequencing of cDNA Clones

Plasmid DNA from both libraries were released from the cells and purified using the REAL Prep 96 plasmid kit (Catalog #26173, QIAGEN, Inc.). The recommended protocol was employed except for the following changes: 1) the bacteria were cultured in 1 ml of sterile Terrific Broth (Catalog #22711, GIBCO-BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool; Altschul, S. F. (1993) J. Mol. Evol 36:290–300; Altschul, S. F. et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases (mammalian (mamp), vertebrate (vrtp), and eukaryote (eukp)) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J.Mol.Evol. 36:290–300; Altschul, S. F. et al. (1990) J.Mol.Evol. 215:403–410) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\ \text{sequence identity} \times \%\ \text{maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding MHCP occurs. Abundance and percent abundance are also reported. Abundance directly reflects the number of times a particular transcript is represented in a cDNA library, and percent abundance is abundance divided by the total number of sequences examined in the cDNA library.

V Extension of MHCP Encoding Polynucleotides

The nucleic acid sequences of the Incyte Clones 2220246 and 3440902 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward"

generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 or SEQ ID NO:4 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the MHCP-encoding sequence, or any part thereof, is used to decrease or inhibit expression of naturally occurring MHCP. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of MHCP, SEQ ID NO:1 or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MHCP-encoding transcript.

IX Expression of MHCP

Expression of MHCP is accomplished by subcloning the cDNAs into appropriate vectors and transforming the vectors into host cells. In this case, the cloning vector is also used to express MHCP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of MHCP into the bacterial growth media which can be used directly in the following assay for activity.

X Demonstration of MHCP Activity

The assay for myosin heavy chain-like proteins is based upon the ability of MHCPs to interact with actinomyosin filaments in vitro (Ho, G. and Chisholm, R. L. (1997) J. Biol. Chem. 272:4522–4527). Actin-activated ATPase is assayed in buffer A (10 mM Tris-HCl, pH 7.6, 25 mM KCl, 5 mM $MgCl_2$, 0.1 mM $CaCl_2$, 1 mM ATP), 0–10 μM MHCP, 0–10 μM actin, and 50 μg/ml myosin. $Ca^{2+}$-activated ATPase is assayed in buffer B (20 mM Tris-HCl, pH 8.0, 500 mM KCl, 10 mM $CaCl_2$, 1 mM ATP), 0–10 μM MHCP, and 50 μg/ml myosin. Reactions are incubated at room temperature for 5 min, quenched with acid, and the liberated inorganic phosphate ($P_i$) is quantified following organic extraction.

In vitro motility assays are performed as follows. Myosin is diluted to 200 μg/ml in buffer C (25 mM imidazole, pH 7.4, 25 mM KCl, 4 mM $MgCl_2$, 1 mM EGTA, 10 mM dithiothreitol), applied to a flow cell coated with nitrocellulose, and blocked with buffer C containing 0.5 mg/ml BSA (C/BSA). A solution of phalloidin-labeled actin is perfused followed by 1 mM ATP in C/BSA to remove myosin heads that bind actin in a rigor fashion. After washing with C/BSA to remove the excess nonfluorescent actin, a solution of rhodamine-phalloidin-labeled actin and MHCP in C/BSA is introduced. Active movement is initiated at room temperature by introducing C/BSA containing 1 mM ATP and oxygen scavenger enzymes. Images (recorded using a Zeiss standard microscope (Zeiss, N.Y.) equipped with a Hamamatsu SIT camera (Hamamatsu, Japan)) of moving myotubes are tracked for up to 30s, and translocation velocities calculated using the myotube centroids to establish initial and final positions for 2s or 4s samples during the continuous movement.

XI Production of MHCP Specific Antibodies

MHCP that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using LASERGENE software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring MHCP Using Specific Antibodies

Naturally occurring or recombinant MHCP is substantially purified by immunoaffinity chromatography using antibodies specific for MHCP. An immunoaffinity column is constructed by covalently coupling MHCP antibody to an activated chromatographic resin, such as CNBr-activated SEPHAROSE (Pharmacia & Upjohn). After the coupling, the resin is blocked and washed according to the manufacturer's instructions.

Media containing MHCP is passed over the immunoaffinity column, and the column is washed under conditions that allow the preferential absorbance of MHCP (e.g., high ionic strength buffers in the presence of detergent). The column is eluted under conditions that disrupt antibody/MHCP binding (eg, a buffer of pH 2–3 or a high concentration of a chaotrope, such as urea or thiocyanate ion), and MHCP is collected.

XIII Identification of Molecules Which Interact with MHCP

MHCP or biologically active fragments thereof are labeled with $^{125}I$ Bolton-Hunter reagent (Bolton et al. (1973)

Biochem. J. 133: 529). Candidate molecules previously arrayed in the wells of a multi-well plate are incubated with the labeled MHCP, washed and any wells with labeled MHCP complex are assayed. Data obtained using different concentrations of MHCP are used to calculate values for the number, affinity, and association of MHCP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding the myosin heavy chain-like protein having the amino acid sequence set forth in SEQ ID NO:1 or SEQ ID NO:3.

2. A composition comprising the polynucleotide sequence of claim 1.

3. An isolated and purified polynucleotide sequence which is complementary to the polynucleotide sequence of claim 1.

4. An isolated and purified polynucleotide sequence comprising the nucleic acid sequence set forth in SEQ ID NO:2 or SEQ ID NO:4.

5. An isolated and purified polynucleotide sequence which is complementary to the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:1 or SEQ ID NO:3, the method comprising the steps of:
   a) culturing the host cell of claim 7 under conditions suitable for the expression of the polypeptide; and
   b) recovering the polypeptide from the host cell culture.

* * * * *